(12) United States Patent
Gitman et al.

(10) Patent No.: US 8,745,825 B2
(45) Date of Patent: Jun. 10, 2014

(54) GRIPPING SLEEVE DEVICE FOR PRECISION INSTRUMENTS

(75) Inventors: Eliot Robert Gitman, Jerusalem (IL); David Joseph Hirsch, Jerusalem (IL)

(73) Assignee: Scalpal LLC, Wilmington, DE (US)

( * ) Notice: Subject to any disclaimer, the term of this patent is extended or adjusted under 35 U.S.C. 154(b) by 480 days.

(21) Appl. No.: 12/620,927

(22) Filed: Nov. 18, 2009

(65) Prior Publication Data

US 2010/0095487 A1    Apr. 22, 2010

Related U.S. Application Data (63) Continuation-in-part of application No. 12/605,729, filed on Oct. 26, 2009, which is a continuation-in-part of application No. 12/275,754, filed on Nov. 21, 2008.

(30) Foreign Application Priority Data

Jul. 20, 2008   (IL) .......................................... 192739

(51) Int. Cl.
    *B25G 1/10* (2006.01)
(52) U.S. Cl.
    USPC .......................................................... 16/430
(58) Field of Classification Search
    USPC .............. 16/430, DIG. 12, DIG. 19; 606/167; 81/526, 427.5, 489; 30/526, 125, 353, 30/356; 15/143.1; 401/6; D19/55, 65, 100
    See application file for complete search history.

(56) References Cited

U.S. PATENT DOCUMENTS

| D101,325 | S |   | 3/1870 | Brown |   |
|---|---|---|---|---|---|
| 796,980 | A | * | 8/1905 | Andrews | ...................... 15/143.1 |

(Continued)

FOREIGN PATENT DOCUMENTS

| EP | 710575 A1 | * | 5/1996 | ........... B43K 23/008 |
|---|---|---|---|---|
| WO | 2010/004541 |  | 1/2010 |  |
| WO | 2013/175463 |  | 11/2013 |  |

OTHER PUBLICATIONS

Office Action issued by U.S. Patent Office on Jul. 6, 2010 in connection with corresponding parent U.S. Appl. No. 12/275,754.

(Continued)

*Primary Examiner* — Victor Batson
*Assistant Examiner* — Matthew Sullivan
(74) *Attorney, Agent, or Firm* — Smith, Gambrell & Russell, LLP

(57) ABSTRACT

The invention provides an ergonomic, gripping sleeve device for precision instruments, comprising a tubular product open at opposite ends thereof and attachable as a sleeve close to a proximal end of said precision instrument having a working tip at its proximal end, said sleeve device being designed to facilitate the positioning of the user's hand grip, said sleeve device comprising a longitudinally extended tubular body substantially hollow and oval in cross-section and being provided on its outer surface with four, substantially concave indentations, a first concave indentation being provided along a top surface of said sleeve device, second and third indentations being provided along lateral surfaces, and a fourth indentation being provided along the bottom surface of said sleeve device, characterized in that the surface of the top of said sleeve device is contoured such that extending from its distal end toward its proximal end and approaching said proximal end there is provided said concave indentation which extends and merges into an elevated surface support which tapers angularly towards said proximal end of said sleeve device, so as to allow for positioning of said user's index finger sufficiently close to said proximal end of said sleeve device and wherein said sleeve device comprises a plurality of sequential ovals of varying width and shape, and wherein said indentations are positioned relative to each other to provide a contiguous interface therebetween and a contiguous interface relative to the user's thumb, index finger and middle finger to facilitate controlled rolling between the user's fingers.

25 Claims, 4 Drawing Sheets

(56) References Cited

U.S. PATENT DOCUMENTS

| | | | |
|---|---|---|---|
| 2,173,451 A * | 9/1939 | Lorber | 401/6 |
| D134,205 S * | 10/1942 | Hasselquist | D19/55 |
| 2,782,764 A | 2/1957 | Lehman, Jr. | 120/102 |
| 3,247,594 A * | 4/1966 | Nosonowitz | 433/102 |
| D223,307 S | 4/1972 | Nockolds | |
| 4,149,811 A | 4/1979 | Coffman | 401/6 |
| 4,167,347 A | 9/1979 | Hoyle | 401/88 |
| D253,219 S | 10/1979 | Meyer | |
| D258,310 S | 2/1981 | LaHaye | |
| D269,357 S * | 6/1983 | Jagger | D19/45 |
| 4,526,547 A * | 7/1985 | Rusk | 434/166 |
| D292,104 S * | 9/1987 | Keller, Jr. | D19/55 |
| D298,439 S * | 11/1988 | Rusk | D19/55 |
| 4,832,604 A * | 5/1989 | Rusk | 434/166 |
| D307,444 S | 4/1990 | Poisson et al. | |
| D307,601 S | 5/1990 | Poisson et al. | |
| D313,624 S * | 1/1991 | Ferjan | D19/55 |
| D318,295 S * | 7/1991 | Sze | D19/55 |
| 5,056,945 A | 10/1991 | Klodt | 401/6 |
| 5,143,463 A * | 9/1992 | Pozil et al. | 401/6 |
| D330,079 S | 10/1992 | Dalling et al. | |
| 5,176,649 A | 1/1993 | Wakabayashi | |
| 5,217,001 A | 6/1993 | Nakao et al. | |
| 5,228,851 A | 7/1993 | Burton | |
| 5,237,984 A | 8/1993 | Williams et al. | |
| D359,758 S | 6/1995 | Inami | |
| D361,345 S * | 8/1995 | Chen | D19/49 |
| 5,440,784 A | 8/1995 | Hull et al. | |
| 5,470,162 A * | 11/1995 | Rubin | 401/6 |
| D372,047 S * | 7/1996 | Adatte et al. | D19/42 |
| 5,531,754 A | 7/1996 | Shackelford, Sr. et al. | |
| D373,143 S * | 8/1996 | Jagger | D19/55 |
| 5,578,050 A | 11/1996 | Webb | |
| 5,626,430 A * | 5/1997 | Bistrack | 401/6 |
| 5,785,443 A * | 7/1998 | Rubin | 401/6 |
| 5,975,909 A | 11/1999 | Ritchie | |
| 5,988,909 A | 11/1999 | Luke, Jr. et al. | 401/6 |
| 6,146,038 A | 11/2000 | Mittersinker et al. | 401/6 |
| D440,605 S * | 4/2001 | Izushima | D19/55 |
| 6,296,409 B1 * | 10/2001 | Cherry et al. | 401/6 |
| 6,315,476 B2 * | 11/2001 | Nakagawa | 401/6 |
| 6,343,885 B1 * | 2/2002 | Heyne | 401/48 |
| D457,630 S | 5/2002 | Lehtonen | |
| 6,390,818 B2 * | 5/2002 | Ferranti | 433/141 |
| 6,408,524 B1 | 6/2002 | Lai | |
| 6,502,314 B1 | 1/2003 | McCatty | |
| 6,554,515 B2 | 4/2003 | Debbas | 401/6 |
| D480,423 S | 10/2003 | Kung | |
| 6,752,555 B2 | 6/2004 | Geddes et al. | 401/6 |
| D499,141 S | 11/2004 | Chevalier | |
| D504,700 S | 5/2005 | Chuang | |
| D512,458 S | 12/2005 | Shiina | |
| D515,389 S | 2/2006 | Hsu | |
| 7,101,382 B2 | 9/2006 | George et al. | |
| D533,944 S | 12/2006 | Sullivan et al. | |
| 7,150,754 B2 | 12/2006 | Ziemer | |
| 7,153,317 B2 | 12/2006 | Kanodia et al. | |
| D535,749 S | 1/2007 | Yaniv et al. | |
| 7,240,390 B2 | 7/2007 | Pfenniger et al. | |
| D560,803 S | 1/2008 | Tasse et al. | |
| D561,828 S * | 2/2008 | Wesselmann et al. | D19/41 |
| D565,106 S | 3/2008 | Silverstein | |
| 7,357,773 B2 | 4/2008 | Watschke | |
| D568,475 S | 5/2008 | Sandel et al. | |
| D589,619 S | 3/2009 | Wu | |
| D590,062 S | 3/2009 | Wu | |
| 7,647,704 B2 | 1/2010 | Petersen | |
| D620,107 S | 7/2010 | Bartlett et al. | |
| D632,391 S | 2/2011 | Gitman | |
| D633,142 S | 2/2011 | Chaffee et al. | |
| D635,260 S | 3/2011 | Gitman | |
| D642,214 S | 7/2011 | Gitman | |
| D651,648 S * | 1/2012 | Luettgens | D19/55 |
| D660,421 S | 5/2012 | Miller et al. | |
| 8,434,954 B2 | 5/2013 | Gitman et al. | |
| D687,950 S | 8/2013 | Gitman | |
| 2002/0124353 A1 | 9/2002 | Holland-Letz | |
| 2002/0170145 A1 | 11/2002 | Stvartak et al. | |
| 2004/0133217 A1 | 7/2004 | Watschke | |
| 2004/0204629 A1 | 10/2004 | Knapp | |
| 2005/0150083 A1 | 7/2005 | Roberts | |
| 2005/0155185 A1 | 7/2005 | Shmueli et al. | |
| 2006/0026800 A1 | 2/2006 | Lawless | |
| 2006/0041266 A1 | 2/2006 | Sullivan et al. | |
| 2006/0075606 A1 | 4/2006 | Lawless | |
| 2006/0252989 A1 | 11/2006 | Bar-Or et al. | |
| 2006/0263142 A1 | 11/2006 | Goldberg | |
| 2007/0156160 A1 | 7/2007 | Petersen | |
| 2008/0051813 A1 | 2/2008 | Dunn | |
| 2008/0163463 A1 | 7/2008 | Hulden | |
| 2009/0187069 A1 | 7/2009 | Terliuc et al. | |
| 2010/0005630 A1 | 1/2010 | Gitman et al. | |
| 2011/0087070 A1 | 4/2011 | Tilson et al. | |
| 2012/0010468 A1 | 1/2012 | Afridi | |

OTHER PUBLICATIONS

Office Action issued by U.S. Patent Office on Jan. 13, 2010 in connection with corresponding parent U.S. Appl. No. 12/275,754.
Office Action issued by U.S. Patent Office on May 30, 2012 in connection with corresponding parent U.S. Appl. No. 12/275,754.
Office Action issued by U.S. Patent Office on Aug. 31, 2011 in connection with corresponding parent U.S. Appl. No. 12/275,754.
Office Action issued by U.S. Patent Office on Mar. 17, 2011 in connection with corresponding parent U.S. Appl. No. 12/275,754.
Office Action issued by the USPTO on Nov. 18, 2013 in parent U.S. Appl. No. 12/275,754.

* cited by examiner

FIG. 4  LEFT

FIG. 5  RIGHT

FIG. 6  TOP

FIG. 7  BOTTOM

GRIPPING SLEEVE DEVICE FOR PRECISION INSTRUMENTS

CROSS-REFERENCE TO RELATED APPLICATIONS

The present specification is a continuation-in-part of co-pending U.S. application Ser. No. 12/605,729, filed Oct. 26, 2009, and entitled "Handle For Writing Instruments" which in turn is a continuation-in-part of co-pending U.S. application Ser. No. 12/275,754, filed Nov. 21, 2008, and entitled "Handle For Surgical And Dental Tools," and Applicants hereby claim priority and the benefit of both these prior applications.

FIELD OF THE INVENTION

The present invention relates to an ergonomic, gripping sleeve device for precision instruments, such as writing instruments and precision surgical and dental tools.

BACKGROUND OF THE INVENTION

The term "writing instruments" as used herein is intended to denote and include all writing instruments, especially those selected from the group consisting of ball point pens, felt-tipped pens, fountain pens, pencils, mechanical pencils, rapidiographs, computer stylus, scoring instruments, engraving tools, and soldering devices.

Furthermore, the term "handles for precision surgical and dental tools" includes electro-surgical devices and surgical devices used in microsurgery.

All of the relevant teachings of each of the above cited parent applications are incorporated herein by reference.

Standard scalpel handles with flat gripping arrangements do not provide contoured gripping surfaces to keep the index finger, thumb and middle finger in place. Moreover, standard scalpel handles with flat body handle gripping arrangements can lead to slippage of the fingers onto the blade or an uncontrolled rolling between the fingers.

Similarly standard writing instruments with round or octagonal gripping arrangements do not provide contoured gripping surfaces to keep the index finger, thumb and middle finger in place. Contrast writing instruments that are round or octagonal or triangular also suffer from this deficiency.

Many innovative handle designs have been implemented in order to address issues related to ergonomic requirements of a grip for a surgical or writing instrument. Thus, there have been several scalpel designs to address the protection of the scalpel user from the danger of the sharp blade. In this regard, attention is directed to the parent applications mentioned above.

While the parent applications deal with improved handles for writing and surgical instruments, their applicability is primarily directed to a new design for the handles themselves. It affords no help for existing precision instruments, like writing and surgical instruments, with standard handles.

Therefore, there is a need in the industry to provide a sleeve that fits over existing handles of precision instruments, like writing and surgical instruments, and provides a superior gripping surface for the user.

DESCRIPTION OF THE PRIOR ART

In Debbas (U.S. Pat. No. 6,554,515) there is described and claimed an ergonomic writing instrument, however as can be seen in FIGS. 4-8 and 18-28 of said patent, the cross-sectional configuration of said handle is substantially triangular.

Referring to Lehman (U.S. Pat. No. 2,782,764) and Coffman (U.S. Pat. No. 4,149,811), these patents also teach writing instruments and writing and engraving instruments, wherein the cross-sectional configuration of the handle is substantially triangular.

In Pozil (U.S. Pat. No. 5,143,463), there is described and claimed a writing aid wherein the cross-sectional configuration of the handle is described as being generally pear-shaped and provides gripping surfaces that keep the fingers in place.

In Rusk (U.S. Pat. No. 4,832,604) there is described and claimed a writing aid, including a body having a central bore for receiving a hand-held writing instrument, and an exterior including a first, second and third gripping surface; however, this adaptor sleeve is also substantially triangular in its cross-sectional configuration.

Hoyle (U.S. Pat. No. 4,167,347) discloses a removable finger grip adaptable to a wide variety and size of writing instruments. The finger grip is an elongate resilient body having a triangular cross-sectional shape and a cylindrical bore coaxial with the longitudinal axis.

Geddes (U.S. Pat. No. 6,752,555) discloses a grip attachment which is a bristle grip in various shapes and sizes.

Webb (U.S. Pat. No. 5,578,050) discloses a handle sleeve for facilitating the use of ophthalmic and micro-surgical instruments. It includes a flexible tube which can be removably attached to the instrument handle. The sleeve preferably has a knurling pattern or a plurality of ridges disposed on its outside surface, to improve traction and tactile feel.

Klodt (U.S. Pat. No. 5,056,945) discloses a grip for a writing instrument which has a resilient plastic hollow tube with a plurality of flexible interior ribs extending radially inwardly from the tube and extending axially the length of the tube. A plurality of flexible exterior ribs extend radially outwardly from the tube and extend axially the length of the tube. The interior ribs are adapted to resiliently engage the shank of a writing instrument and the exterior ribs are preferably tapered and provide a resilient, cushioning grip to a writer.

Mittersinker (U.S. Pat. No. 6,146,038) discloses a hand instrument with variable grip arrangement and has an instrument body of the type to be held between the fingers of the hand for use, the body having an active end and an opposite end. A resilient material forms a grip around the body near the active end. Radial expansion beams are under the grip for bending radially outwardly for expanding the grip into an expanded ergonomic position and for resiliently returning to a straightened condition for contracting the grip into a contracted storage position. Cams or threads or other mechanisms engage the beams for moving them between the expanded and the contracted positions with rotation of a part of the instrument body.

Luke (U.S. Pat. No. 5,988,909) discloses a writing instrument having a tubular shaft. A grip is provided having a contoured surface for facilitating manual gripping of the writing instrument. The grip is axially aligned with, and attached to one end of, the shaft.

While alleviating many of the problems related to efficiently using a writing instrument, such as positioning and maintaining a desired grip, the sleeves and grips disclosed in the prior art inventions do not adequately address the need to minimize the fatigue due to the need to adjust relative position of fingers and maintain an assured operational control and alignment of the writing instrument during writing.

Flat or triangular shaped devices are not comfortable for the user, as these handles do not sufficiently cater to the ergonomic requirements of a grip. Flat body handles provide textured gripping surfaces for the fingers, but are sometimes too small or too narrow to grip comfortably for extended periods of time, or once gripped restrict the free movement of the hand. Furthermore, flat body handle gripping arrangements can only be used basically in one position without the danger of slippage or rolling between the fingers accompanied by the risk of consequent injury to the user or the patient. Grips having triangular cross-sections may present an ease of orientation positioning, however, they fall short of providing ergonomically comfortable working solutions. One edge of the triangular shaped device can dig into a user's finger.

While alleviating many of the problems related to efficiently using an instrument, such as positioning and maintaining a desired grip, the sleeves and grips disclosed in the prior art do not adequately address the need to minimize the fatigue due to the need to adjust relative position of fingers and maintain an assured operational control and alignment of, for example, the scalpel blade during surgery, and, furthermore, these grips do nothing to eliminate the need for additional personnel to maintain whatever mechanical, or sanitary features of the prior art.

Therefore, there is a need in the industry for a sleeve for a handle for precision instruments, like a medical or writing instrument, which allows the instrument to be gripped comfortably for long periods of time, and to be gripped in alternative positions.

BRIEF DESCRIPTION OF THE INVENTION

Therefore the objectives of the present invention are to obviate the disadvantages of prior art sleeves for precision instrument handles and to provide a sleeve for a precision instrument handle which has uniquely spaced indentations that accommodate finger form rather than finger pressure, thereby allowing the instrument to be gripped comfortably for long periods of time, and to be gripped in alternative positions.

The present invention achieves the above objectives by providing an ergonomic, gripping sleeve device for precision instruments, comprising a tubular product open at opposite ends thereof and attachable as a sleeve close to a proximal end of said precision instrument having a working tip at its proximal end, said sleeve device being designed to facilitate the positioning of the user's hand grip, said sleeve device comprising a longitudinally extended tubular body substantially hollow and oval in cross-section and being provided on its outer surface with four, substantially concave indentations, a first concave indentation being provided along a top surface of said sleeve device, second and third indentations being provided along lateral surfaces, and a fourth indentation being provided along the bottom surface of said sleeve device, characterized in that the surface of the top of said sleeve device is contoured such that extending from its distal end toward its proximal end and approaching said proximal end there is provided said concave indentation which extends and merges into an elevated surface support which tapers angularly towards said proximal end of said sleeve device, so as to allow for positioning of said user's index finger sufficiently close to said proximal end of said sleeve device and wherein said sleeve device comprises a plurality of sequential ovals of varying width and shape, and wherein said indentations are positioned relative to each other to provide a contiguous interface therebetween and a contiguous interface relative to the user's thumb, index finger and middle finger to facilitate controlled rolling between the user's fingers.

In preferred embodiments of the present invention, the four indentations are spaced about 90° apart from each other.

Preferably the longitudinally extending body of the sleeve has an axis and said first concave indentation is cut deeper into said body towards said axis than at least one of said other indentations.

As stated hereinbefore, said writing instrument is selected from the group consisting of ball point pens, felt-tipped pens, fountain pens, pencils, mechanical pencils, rapidiographs, computer stylus, scoring instruments, engraving tools, and soldering devices.

Some embodiments include that the sleeve is sterilizable, for example, as will be useful in association with a scalpel as herein described.

In some embodiments, the sleeve will accommodate being used to replace an existing sleeve, due to its versatility in incorporation.

As will be realized and understood from the description of the invention hereinafter with reference to the Figures, the sleeve for the handle of a precision instrument of the present invention has many advantages over prior art instrument handles and sleeves for handles in that it can be held effortlessly without excessive pressure, can be spun to give a new position, unlike standard instruments. Furthermore, as described hereinafter, it can be held in at least four different positions with the user gravitating to the most comfortable position.

Other objects, features and advantages of the present invention will become apparent upon reading the following detailed description in conjunction with the drawings and the claims.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. May be shorter, longer, thicker, thinner—to adjust to different sized hands.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

As shown in FIGS. 10A-10D, the ergonomic sleeve 4 of this invention fits over the handle 1 of the precision instrument. While two types of precision instruments are shown, it may be appreciated that the sleeve may be used with any type of handle of any type of instrument.

Figure 10A:
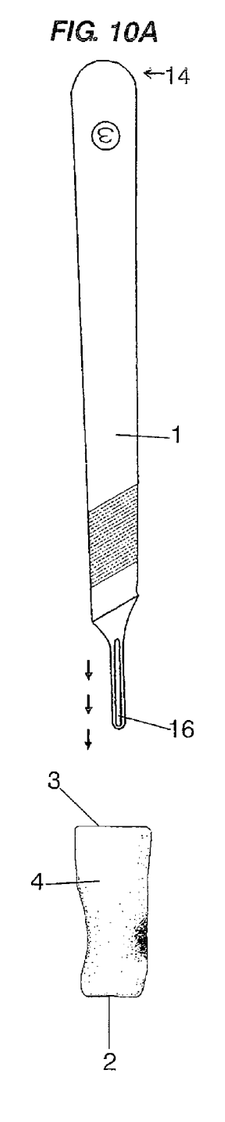
FIGS. 10A, 10B, 10C and 10D show installation of the sleeve on the handle of a writing instrument and on the handle of a surgical instrument.
Figure 10B:
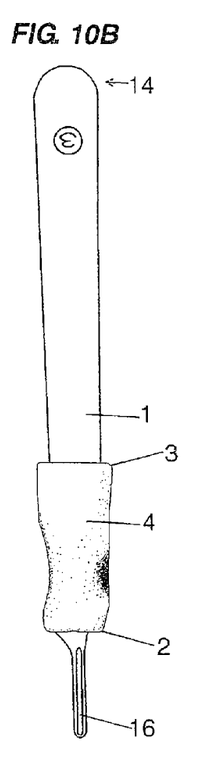

In FIGS. 10A and 10B a scalpel 14 is shown. To use the sleeve of this invention, the sleeve is brought near the blade holder 16 of the scalpel (FIG. 10A). Then (as shown in FIG. 10B) the sleeve is slid over the blade holder and onto the body of the handle 1 of the scalpel. The proximal end 2 of the sleeve is near the blade holder 16 end of the scalpel, whereas the distal end 3 of the sleeve is nearer the middle or distal end of the handle of the scalpel.

Figure 10C:
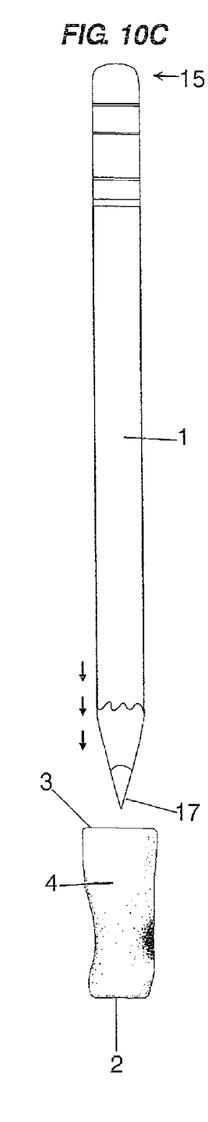
Figure 10D:
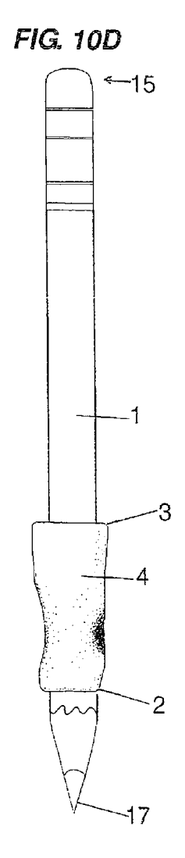

In FIGS. 10C and 10D a writing instrument 15 is shown. To use the sleeve of this invention, the sleeve is brought near the writing tip 17 of the writing instrument (FIG. 10C). Then (as shown in FIG. 10D) the sleeve is slid over the writing tip and onto the body of the handle 1 of the writing instrument. The proximal end 2 of the sleeve is near the writing tip 17 end of the writing instrument, whereas the distal end 3 of the sleeve is nearer the middle or distal end of the handle of the writing instrument.

By like manner, the sleeve may be used with any type of handle of any type of instrument, though generally the invention is intended for use with precision instruments.

Figure 1:
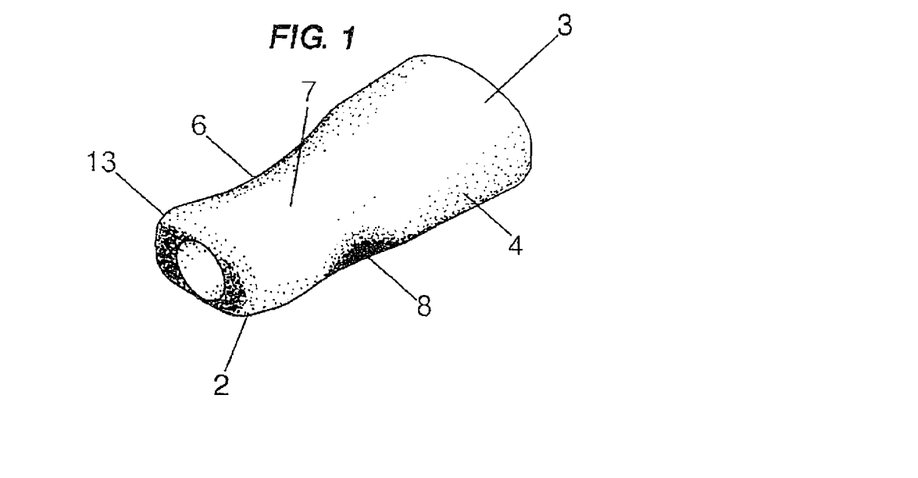
FIG. 1 is a perspective view of a preferred embodiment of the sleeve for a precision instrument handle according to the invention.
Figure 2A:
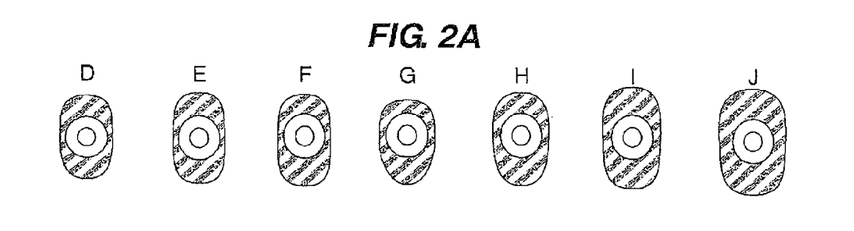
FIG. 2A are sectional views of the sleeve taken at different points along its length as shown in FIG. 2B.
Figure 2B:
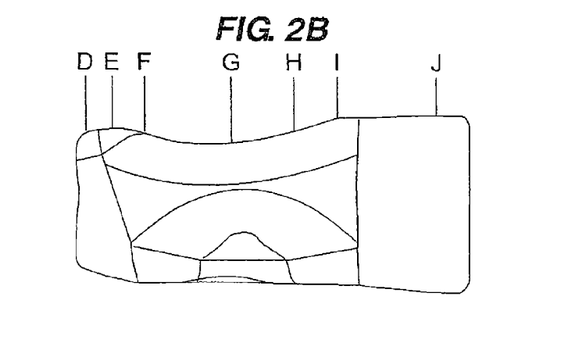
FIG. 2B is a view of the sleeve showings its indentions and contour.
Figure 3:
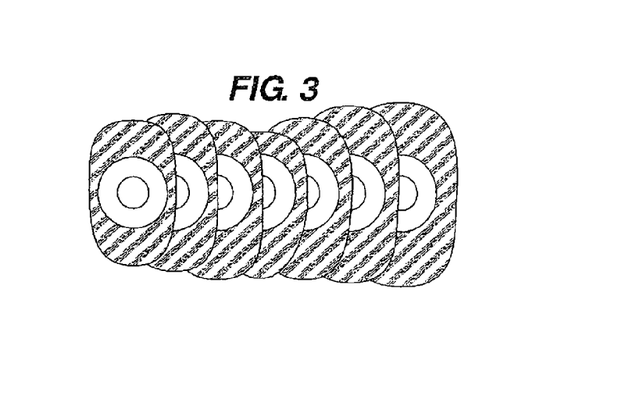
FIG. 3 is a Z series compilation of the sectional views of FIG. 2A
Figure 4:
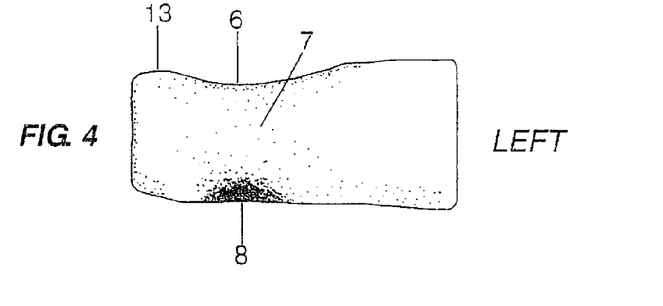
FIG. 4 is a left side view of the sleeve for an instrument handle according to the invention, showing one of the lateral indentations and the top and bottom indentations.
Figure 5:
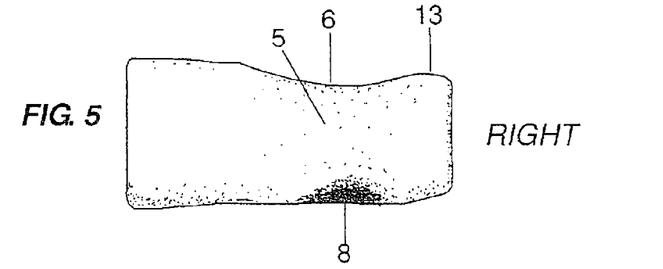
FIG. 5 is a right side view of the sleeve for an instrument handle according to the invention, showing one of the lateral indentations and the top and bottom indentations.
Figure 6:
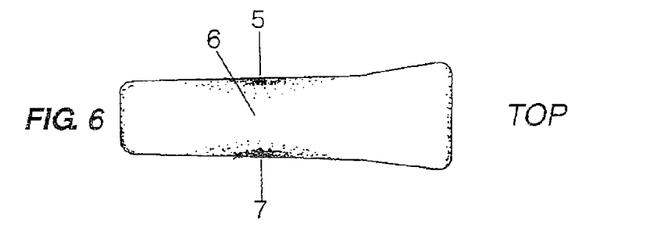
FIG. 6 is a top side view of the sleeve for an instrument handle according to the invention, showing the top indentation and the lateral indentations.
Figure 7:
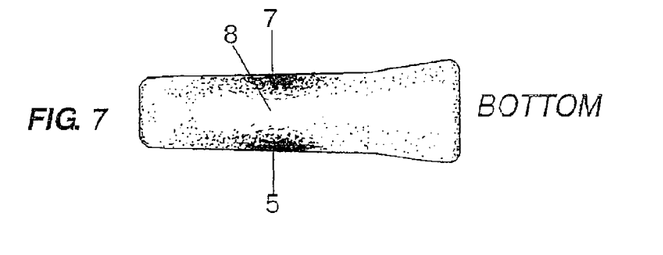
FIG. 7 is a bottom side view of the sleeve for an instrument handle according to the invention, showing the bottom indentation and the lateral indentations.
Figures 8A, 8B:
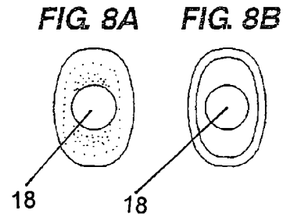
FIG. 8A is the proximal end view of the handle according to the invention and FIG. 8B is the distal end view of the handle according to the invention, where the embodied handle contains a central bore 18 to accommodate the writing instrument or other appropriate tool
Figures 9A, 9B:
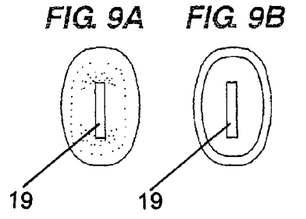
FIG. 9A is the proximal end view of the handle according to the invention and FIG. 9B is the distal end view of the handle according to the invention, where the embodied handle contains a central slot 19 to accommodate a scalpel or other appropriate tool.

There is seen in FIG. 1 the sleeve 4 for a handle for a precision instrument handle comprising a longitudinally extending body which is formed inter alia of sequential ovals D, E, F, G, H, I, J, etc., as seen in FIGS. 2A, 2B and 3, of varying width and shape. The body of the sleeve has four concave indentations 5 (not visible in FIG. 1), 6, 7, and 8 moldably formed thereinto, and adjoining the proximal end of the sleeve.

The surface of the top of sleeve is contoured such that extending from its distal end toward its proximal end and approaching said proximal end there is provided the concave indentation 6 which extends and merges into an elevated ridge-like surface support which tapers angularly towards the proximal end of said handle, so as to allow for positioning of the user's index finger sufficiently close to the proximal end of the sleeve.

In preferred embodiments of the present invention, the four indentations are spaced about 90° apart from each other.

According to one embodiment of the present invention, as seen with reference to FIGS. 1, 11A and 11B, the indentations 5 and 8 are designed to accommodate the side of middle finger 11, indentation 6 is designed to accommodate the index finger 9, and indentation 7 and indentation 8 in part are designed to accommodate the thumb 10, as explained in the following paragraph, thereby facilitating gripping by a user. The user's fingers are free from being confined to the grip positions of the handle when in use. The general configuration of the indentations according to the present embodiment of the invention allows for the user to comfortably grip the sleeve 4 for the handle in various gripping positions. In other words. the four indentations are substantially axially aligned.

Figure 11A:
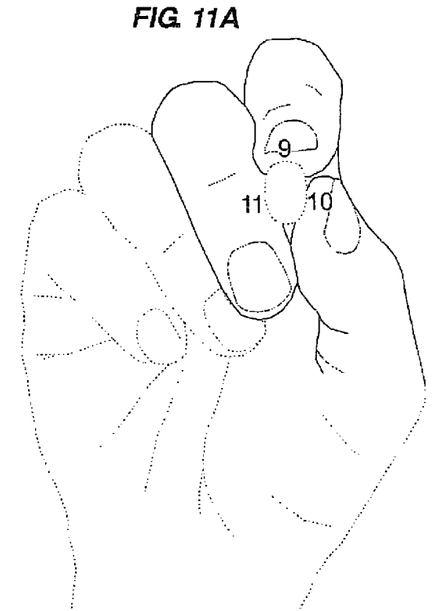
FIGS. 11A and 11B are front views of a hand holding a precision instrument by means of the herein ergonomic sleeve according to the present invention.
Figure 11B:
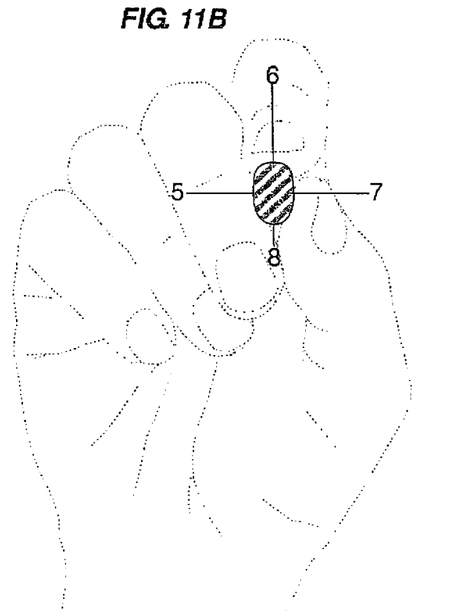

According to one embodiment of the invention, the top indentation 6 as illustrated in FIGS. 1, 11A and 11B is designed to accommodate the index finger 9 of a right handed user. The lateral indentation 7 as illustrated in FIGS. 1, 11A and 11B is designed to accommodate the thumb 10 of the user.

The bottom indentation 8 as illustrated in FIGS. 1, 11A, and 11B is designed to accommodate a portion of the middle finger 11 of the user and a portion of the thumb 10. The lateral indentation 5 as illustrated in FIGS. 11A and 11B, is designed to also accommodate a portion of the middle finger 11 of the user. The positioning of the lateral indentations is reversed in the case of a left-handed user. Thus, the accommodation of the lateral indentations for the middle finger and the thumb involve the engagement of the same parts of the said middle finger and thumb as detailed above in respect to the right handed user.

Thus, e.g., for a standard right handed user, a first position could be with indentation 5 accommodating middle finger 11, indention 6 accommodating index finger 9, indentation 7 and 8 accommodating the thumb 10 wherein indentation 8 also accommodates a portion of middle finger 11 as seen in FIGS. 11A and 11b.

If the user finds the same to be more comfortable, he can rotate the instrument with the sleeve attached thereto by 90 degrees, to obtain a second writing position wherein indentation 5 accommodates both a portion of the middle finger and the thumb, indentation 6 accommodates a further portion of the middle finger, indentation 7 accommodates the index finger and indentation 8 accommodates the thumb.

By further rotating the instrument ad the sleeve attached therto, there can be achieved a third position in which indentation 5 accommodates a portion of the thumb, indentation 6 accommodates a portion of the middle finger and a further portion of the thumb. Indentation 7 accommodates a further portion of the middle finger and indentation 8 accommodates the index finger.

With a further rotation, there is achieved a fourth position in which indentation 5 accommodates the index finger, indentation 6 accommodates a portion of the thumb, indentation 7 accommodates a portion of the middle finger and a portion of the thumb, and indentation 8 accommodates a further portion of the middle finger.

The top concave indentation 6 has a preferred maximum depth of about 2.0 mm below the surface of the sleeve, which is preferably slightly deeper than the lateral indentations 5 and 7 which have a preferred maximum depth of about 1.0 mm and the bottom indentation 8, which has a preferred maximum depth of about 0.3 mm at its lowest point.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An ergonomic, gripping sleeve device for precision instruments, comprising a tubular product open at opposite ends thereof and attachable as a sleeve close to a proximal end of said precision instrument having a working tip at its proximal end, said gripping sleeve device being designed to facilitate the positioning of the user's hand grip, said gripping sleeve device comprising a longitudinally extended tubular body substantially hollow and oval in cross-section and being provided on its outer surface with four, substantially concave indentations that include a first concave indentation provided along a top surface of said gripping sleeve device, which first concave indentation extends and merges into an elevated ridge-like surface support that is proximally positioned relative to the first concave indentation, second and third indentations being provided along lateral surfaces, and a fourth indentation being provided along the bottom surface of said gripping sleeve device, and wherein the substantially hollow and oval in cross-section tubular body comprises, along a longitudinal length of said tubular body, a plurality of sequential oval cross-sections of varying width and shape and each with an oval major diameter axis extending in a top to bottom direction, and wherein said indentations are positioned relative to each other to provide a contiguous interface therebetween and a contiguous interface relative to the user's thumb, index finger and middle finger to facilitate controlled rolling between the user's fingers, and wherein said second and third indentations are more predominantly located on lower portions of the lateral surfaces.

2. An ergonomic sleeve device according to claim 1 wherein the four indentations are spaced about 90° apart from each other, with the second and third indentations each having an upper portion aligned with a minor axis of the cross-section and a maximum depth positioned in the lower portion of the lateral sides.

3. An ergonomic sleeve device according to claim 1 wherein said sleeve device has a central axis and said first concave indentation is cut deeper into said body towards said axis than at least one of said other indentations.

4. An ergonomic sleeve device according to claim 1 configured for use in combination with a writing instrument wherein said writing instrument is selected from the group consisting of ball point pens, felt-tipped pens, fountain pens, pencils, mechanical pencils, rapidiographs, computer stylus; scoring instruments, engraving tools, and soldering devices.

5. An ergonomic sleeve device according to claim 1 configured for use in combination with a precision, surgical or dental tool including electro-surgical devices and surgical devices used in microsurgery.

6. An ergonomic sleeve according to claim 1, wherein said gripping sleeve has a longitudinally extending through-hole, and said through-hole is dimensioned for removable longitudinal placement over a handle of a precision instrument.

7. An ergonomic sleeve according to claim 6, wherein said first, top indentation is formed on a top portion of said body of said sleeve so as to define a curved end portion in a vertical cross-sectional plane extending perpendicular to a central axis of said sleeve, and said fourth, bottom indentation is formed on a bottom portion of said body of said sleeve so as to also define a curved end portion in the vertical cross-sectional plane.

8. An ergonomic sleeve according to claim 1, wherein one of the second and third lateral indentations extends into the bottom indentation such that said one of said second and third lateral indentations and said bottom indentation define together a continuous middle finger reception cavity comprised of a portion of that one of the lateral indentations and a portion of the bottom indentation, and said top indentation is configured for accommodating an index finger of said user, and the other of said lateral indentations is configured for accommodating a thumb of said user.

9. An ergonomic sleeve according to claim 7, wherein one of the lateral indentations is configured for accommodating both a portion of a middle finger and a thumb of a user, said top indentation being configured for accommodating a further portion of said middle finger of said user, the other of said lateral indentations being configured for accommodating an index finger of said user and said bottom indentation being configured for accommodating said thumb of said user.

10. An ergonomic sleeve according to claim 7, wherein one of the second and third lateral indentations is configured for accommodating a portion of a thumb of a user, said top indentation being configured for accommodating a portion of a middle finger and a further portion of said thumb of said user, the other of said lateral indentations being configured for accommodating a further portion of said middle finger of said user and said bottom indentation being configured for accommodating an index finger of said user.

11. An ergonomic sleeve according to claim 7, wherein one of the second and third lateral indentations is configured for accommodating an index finger of a user, said top indentation being configured for accommodating a portion of a thumb of said user, the other of said lateral indentations being configured for accommodating a portion of a middle finger and a portion of said thumb of said user, and said bottom indentation being configured for accommodating a further portion of said middle finger of said user.

12. An ergonomic sleeve according to claim 7, wherein said top indentation having a maximum depth of 2.0 mm below a surface of the sleeve, said lateral indentations having a maximum depth of 1.0 mm below a surface of the sleeve and said bottom indentation having a maximum depth of about 0.3 mm below a surface of the sleeve.

13. An ergonomic sleeve according to claim 7, wherein a top surface of said sleeve is contoured, and wherein said top indentation is concave and extending from a distal end of said sleeve toward a proximal end of said sleeve, and wherein said elevated ridge-like surface support has a proximal side tapering angularly down towards said proximal end of said handle.

14. An ergonomic sleeve according to claim 6, said indentations being spaced 90° apart from each other, with the second and third indentations having an upper portion aligned with a minor axis of the cross-section and a maximum depth positioned in a respective lower portion of the lateral sides.

15. An ergonomic sleeve device according to claim 1, wherein a distance between opposing, interior-most surfaces of said first and fourth concave indentations is greater than a lateral spacing distance of said second and third lateral surfaces at a common axial location on said sleeve.

16. An ergonomic sleeve device according to claim 1, wherein, on opposing sides of a horizontal cross-section plane extending through the lateral second and third sides and along a longitudinal central axis of extension of said gripping sleeve, there is defined a non-symmetrical relationship in the oval cross-section positioned at the maximum depth of the first concave indentation.

17. An ergonomic, gripping sleeve device for precision instruments, comprising a tubular product open at opposite ends thereof and attachable as a sleeve close to a proximal end of said precision instrument having a working tip at its proximal end, said gripping sleeve device being designed to facilitate the positioning of the user's hand grip, said gripping sleeve device comprising a longitudinally extended tubular body substantially hollow and oval in cross-section and being provided on its outer surface with four, substantially concave indentations that include a first concave indentation being provided along a top surface of said gripping sleeve device, which first concave indentation extends and merges into an elevated ridge-like surface support, second and third indentations being provided along lateral surfaces, and a fourth indentation being provided along the bottom surface of said gripping sleeve device, and wherein a distance between opposing, interior-most surfaces of said first and fourth concave indentations is greater than a lateral spacing distance of said second and third lateral surfaces at a common axial location on said sleeve, and wherein said gripping sleeve device comprises a plurality of sequential oval cross-sections of varying width and shape, and wherein said indentations are positioned relative to each other to provide a contiguous interface therebetween and a contiguous interface relative to the user's thumb, index finger and middle finger to facilitate controlled rolling between the user's fingers, and wherein said second and third indentations each have a maximum depth positioned in a respective lower half of the lateral sides.

18. An ergonomic sleeve device according to claim 17, wherein, on opposing sides of a horizontal cross-section plane extending through the lateral second and third sides and along a longitudinal central axis of extension of said gripping sleeve, there is defined a non-symmetrical relationship in the oval cross-section positioned at the maximum depth of the first concave indentation.

19. An ergonomic, gripping sleeve device for precision instruments, comprising a tubular product open at opposite ends thereof and attachable as a sleeve close to a proximal end of said precision instrument having a working tip at its proximal end, said gripping sleeve device being designed to facilitate the positioning of the user's hand grip, said gripping sleeve device comprising a longitudinally extended tubular body substantially hollow and oval in cross-section and being provided on its outer surface with four, substantially concave indentations that include a first concave indentation being provided along a top surface of said gripping sleeve device, which first concave indentation extends and merges into an elevated ridge-like surface support, second and third indentations being provided along lateral surfaces, and a fourth indentation being provided along the bottom surface of said gripping sleeve device, and wherein, on opposing sides of a horizontal cross-section plane extending through the lateral second and third surfaces and along a longitudinal central axis of extension of said gripping sleeve, there is defined a non-symmetrical relationship in the oval cross-section positioned at the maximum depth of the first concave indentation; and
wherein said gripping sleeve device comprises in sequence along the longitudinal axis of extension, a plurality of oval cross-sections of varying width and shape, and wherein said indentations are positioned relative to each other to provide a contiguous interface therebetween and a contiguous interface relative to the user's thumb, index finger and middle finger to facilitate controlled rolling between the user's fingers, and
wherein, relative to the oval cross-section positioned at the maximum depth of the first concave indentation, a bottom side of the oval cross-section converges inward more so than a top side.

20. An ergonomic sleeve device according to claim 19, wherein the second and third indentations are positioned predominately in the bottom side of the oval cross section positioned at the maximum depth of the first concave indentation and converge with the bottom indentation such that there is provided a common, extended middle finger reception region comprising a portion of one of said second and third indentations and a portion of the fourth indentation and a thumb reception region comprising the other of said second and third indentations and another portion of the fourth indentation.

21. An ergonomic sleeve device according to claim 19, wherein lateral side portions defining the second and third indentations, in the oval cross-section positioned at the maximum depth of the first concave indentation, converge downwardly toward one another to merge with the bottom indentation and to also, together, define a continuous bottom curve within the oval cross-section at the maximum depth of the first concave indentation.

22. An ergonomic sleeve device according to claim 21, wherein the interface between an upper end of one of the second and third indentations and the top indentation is contiguous across a lateral side, longitudinally extending ridge region representing a maximum outer surface of the lateral side.

23. An ergonomic sleeve device according to claim 17, wherein lateral side portions defining the second and third indentations, in the oval cross-section positioned at the maximum depth of the first concave indentation, converge downwardly toward one another to merge with the bottom indentation and to also, together, define a continuous bottom curve within the oval cross-section at the maximum depth of the first concave indentation.

24. An ergonomic sleeve device according to claim 23, wherein the interface between an upper end of one of the second and third indentations and the top indentation is contiguous across a lateral side, longitudinally extending ridge region representing a maximum outer surface of the lateral side.

25. An ergonomic sleeve device according to claim 6, wherein the longitudinally extending through-hole has a greater top to bottom length than a lateral side to side length.

* * * * *